US007939807B2

(12) United States Patent
Soluri et al.

(10) Patent No.: US 7,939,807 B2
(45) Date of Patent: May 10, 2011

(54) SCINTIGRAPHIC DEVICE WITH SPATIAL SUPER-RESOLUTION

(75) Inventors: Alessandro Soluri, Rome (IT); Roberto Massari, Rome (IT)

(73) Assignee: CNR Consiglio Nazionale delle Richerche, Rome (IT)

( * ) Notice: Subject to any disclaimer, the term of this patent is extended or adjusted under 35 U.S.C. 154(b) by 68 days.

(21) Appl. No.: 12/467,566

(22) Filed: May 18, 2009

(65) Prior Publication Data

US 2010/0090120 A1     Apr. 15, 2010

(30) Foreign Application Priority Data

Oct. 10, 2008    (IT) .............................. M12008A1798

(51) Int. Cl.
*G01T 1/20*        (2006.01)
(52) U.S. Cl. ...................................... 250/369
(58) Field of Classification Search ............... 250/363.1, 250/369, 370.01–370.15; 378/147, 98.8
See application file for complete search history.

(56) References Cited

U.S. PATENT DOCUMENTS

| | | | | |
|---|---|---|---|---|
| 3,612,865 A | * | 10/1971 | Walker | 250/366 |
| 4,259,578 A | * | 3/1981 | Thompson | 250/363.03 |
| 4,419,763 A | * | 12/1983 | Hawman | 378/149 |
| 4,598,203 A | * | 7/1986 | Umetani et al. | 250/366 |
| 5,742,060 A | * | 4/1998 | Ashburn | 250/370.09 |
| 2003/0197127 A1 | * | 10/2003 | Wainer et al. | 250/363.02 |
| 2004/0066904 A1 | * | 4/2004 | Eberhard et al. | 378/147 |

OTHER PUBLICATIONS

Uzunov et al., "Measuring the imaged-object distance with a stationary high-spatial-resolution scintillation camera," 2006, Physics in Medicine and Biology, vol. 51, pp. N199-N204.*
Uzunov et al., "Localizing the Imaged-Object position by stationary position-sensitive scintillation camera using tilted-collimator technique," 2006, IEEE Nuclear Science Symposium Conference Record, vol. M14-54, pp. 2997-2999.*

* cited by examiner

*Primary Examiner* — David P Porta
*Assistant Examiner* — Kiho Kim
(74) *Attorney, Agent, or Firm* — Young & Thompson

(57) ABSTRACT

A scintigraphic device includes: a collimator for receiving and directing electromagnetic radiation from a source; a scintillation structure associated with the collimator for receiving the electromagnetic radiation from the collimator and converting it into visible radiation; an electro-optical converter combined with a suitable electronics and associated with the scintillation structure for receiving the visible radiation and converting it into electric signals; a processing unit connected to the electro-optical converter for receiving the electric signals and rebuilding, as a function of the electric signals, images of the source; an actuating system for mutually moving the source and the collimator to enable the collimator to detect the electromagnetic radiation at different mutual positioning locations of the source and the collimator, the processing unit being adapted to rebuild a plurality of auxiliary images representative of the source, each auxiliary image corresponding to a respective mutual positioning of the source and the collimator.

16 Claims, 7 Drawing Sheets

SCINTIGRAPHIC DEVICE WITH SPATIAL SUPER-RESOLUTION

FIELD AND BACKGROUND OF THE INVENTION

The present invention relates to a spatial super-resolution scintigraphic device.

DESCRIPTION OF THE RELATED ART

It is known that scintigraphic devices generally comprise a collimator, a scintillation structure, one or more photo multiplier tubes and suitable electronic circuits used for image rebuilding.

The function of the collimator is to detect and select photons to a predetermined frequency, which photons are representative of the interaction between the incident radiation and a body that has to be examined; the scintillation structure receives, as an input, the photons selected by the collimator and converts them into visible light. The photo multiplier tubes and said electronic circuits carry out conversion of the light radiation supplied by the scintillation structure into electric signals and, starting from these electric signals, rebuilding of a digital representation of the body that has to be examined.

In order to understand the intrinsic features determining the accuracy and precision degree obtainable in the scintigraphic images, it is necessary to determine the value of the spatial resolution, which value depends on the initial construction choices of the detection system.

For instance, these parameters can depend on the sizes of the crystals used which form the scintillation structure and also on the collimator's sizes and features.

Generally, the configurations that can be used for scintillation crystals can vary in a very wide manner, as a function both of the light yield resulting from scintillation with interacting photons, and of geometric use considerations, such as exactly the sizes thereof.

For instance, the choice of using crystal matrices or a single continuous crystal can be taken into account also in combination with other construction choices that may concern collimators, for example. As a direct result of the above, this involves an efficiency value of the detection system that often takes a fundamental importance in planning said systems. In this regard, by virtue of the fact that in the crystal matrices there is a dead separation region due to the presence of reflecting material between the individual elements, the system efficiency tends to be lower than when a continuous crystal is used.

The assembly of all the adopted solutions determines all the intrinsic features on the spatial resolution of the detection structure thus formed.

Consequently, the device has a total spatial resolution that is the result of the different contributions arising from the technical choices adopted.

Generally, this spatial resolution value depends on the intrinsic resolution of the device $R_i$, and on a contribution connected with the resolution $R_c$ depending on the collimator. The total spatial resolution of the device can therefore be defined by the following relation:

$$R_S = \sqrt{R_i^2 + R_c^2}$$

Actually, in PET applications the restrictive contribution of the mechanical collimation is absent because it is replaced by a principle of collimation connected with the coincidence technique by which the events of antiparallel photons are simultaneously registered. This therefore involves the absence of the collimator's contribution in terms of total resolution on the device, which restriction is also present in traditional SPECT techniques.

Documents U.S. Pat. No. 6,734,430 (Soluri et al.) and U.S. Pat. No. 6,608,310 (Soluri et al.), in addition to WO 96/37791 (De Notaristefani et al.), U.S. Pat. No. 5,783,829 (Sealock et al.), and U.S. Pat. No. 5,864,141 (Stan Majewski et al.), propose improvements in terms of expected spatial resolution.

For instance, in order to improve the performance of the devices, use of particular phototubes is known such as the PSPMT's (Position Sensitive Photo Multiplier Tubes) capable of adding important advantages to the collection modalities of the events that have reached the detector. In addition, the choice of the crystals to be coupled to geometries of the collimator's holes is of fundamental importance for improving the device performance.

At all events, all restrictions connected with the choice of the crystal-collimator coupling have an influence on the intrinsic spatial resolution value of the device. As previously mentioned, the spatial resolution of a detector, not only depends on the choice of the sizes of the collimator's holes and of the collimator's length, but is also dependent on the choice of the sizes of the individual detection elements, should a scintillation matrix or a group of semi-conductor elements be used.

Document U.S. Pat. No. 7,274,022 discloses a method of enabling the collimator's length to be varied so as to avoid physical replacement of same, this parameter allowing the final spatial resolution to be improved.

Generally, the choice of the sizes of the collimator's holes and the choice of the collimator's length, in addition to the sizes of the individual crystal elements (or semi-conductors) give rise to such physical conditions that the final result of expected spatial resolution is limited to a predetermined value.

At the same manner, if it were possible to dynamically change the size of the collimator's holes and the area of the individual detection elements (scintillation crystals or semi-conductors), this variants would produce an important improvement in terms of intrinsic spatial resolution.

However, these dynamic changes, in relation to the sizes of the collimator's holes and the variation in the sizes of the detection elements (crystals or semi-conductors) as highlighted above, appear to be of difficult practical application unless equivalent alternative solutions are used that can lead to obtaining an overall improvement of the spatial resolution, without necessarily resorting to the modification of these parameters.

Generally, therefore, once the physical sizes of the hole width and the lengths of the collimator have been defined, a concrete possibility presently available for obtaining important improvements in the spatial resolution consists in replacement of the whole collimator with selection of the hole sizes and the length in an optimized manner.

This involves a change in the detector features in terms of expected spatial resolution, but this can only take place by physical replacement of the collimator with another one having given and predetermined features.

Generally this possibility is contemplated by the present scintigraphic systems; in fact, there are sets of collimators different from each other, with which some commercial gamma cameras are equipped, exactly for the purpose of enabling selection of the most appropriate collimator depending on clinical requirements.

Therefore, there are general-purpose collimators, of the high-resolution type, i.e., having a spatial resolution with a lower numeric value or with a high detection efficiency which accomplish this task by physical replacement of the collimator, thus helping in improving the spatial resolution or efficiency of the detector.

Other possible alternative solutions consist in use of pinhole collimators with coded opening, introducing ameliorative elements in the spatial resolution, also used in replacement of standard collimation systems. These solutions, often proposed also in Astrophysics allow the spatial resolution value to be improved, but do not use the standard technique of the collimators with parallel holes.

The collimator features take into account some parameters such as length and width of the holes. Therefore, in order to obtain a greater efficiency it is necessary to have bigger hole sizes, while in order to obtain a better spatial resolution it is necessary to have a collimator of greater length and smaller holes.

For instance, if the diagnostic analysis concerns organs the distance of which from the detector increases, in accordance with this principle it will be necessary to use a collimator of appropriate length, of the high resolution type.

Generally, this choice involves, as a consequence, definition of a parameter producing direct effects on the diagnostic capability of the gamma camera.

While this chance is a useful variant for optimizing the gamma camera performance, often this operation is not easy because collimators are often very bulky and heavy. Replacement takes place manually or automatically, with exchange of a previously existing collimator that is replaced with another of suitable features.

However, this procedure introduces idle times between measurements and operation, and it often appears to be very complicated in terms of efficiency of the operating control of the scintigraphic machine.

Exactly due to this operating difficulty, often mounting of general-purpose collimators is selected as the standard solution, which collimators integrate suitable features for maintaining the spatial resolution with a hole size adapted to obtain a good detection efficiency of the device.

A much more complicated problem, in cameras utilizing crystal matrices or semi-conductors for example, appears to be that of changing the sizes of the pixels of which the detection matrix is made in a dynamic manner, this constituting a current limitation in the possibility of modifying the expected spatial resolutions.

In addition, very difficult is the availability of solutions capable of enabling a dynamic variation in the finished sizes of crystals or semi-conductor elements, so as to improve the spatial resolution, during a scintigraphic examination.

Objects

Accordingly, it is an aim of the present invention to make available a scintigraphic device in which a better spatial resolution than that imposed by the physical and construction limits of the device itself is obtained.

It is a further aim of the invention to provide a scintigraphic device in which the spatial resolution can be improved without resorting to modifications or replacements in the initial detection structure.

Another aim of the invention is to make available a scintigraphic device that is able to carry out detection operations to different resolutions, without substantial modifications to the device itself being required.

SUMMARY OF THE INVENTION

The foregoing and further aims are substantially achieved by a super-resolution scintigraphic device in accordance with that which is described in the appended claims.

Further features and advantages will become more apparent from the detailed description of a preferred but not exclusive embodiment of the invention.

BRIEF DESCRIPTION OF THE DRAWINGS

This description is taken hereinafter with reference to the accompanying drawings, given by way of non-limiting example, in which:

FIGS. 3b-3c show details concerning the diagram in FIG. 3a;

DESCRIPTION OF THE PREFERRED EMBODIMENT

Figure 1:
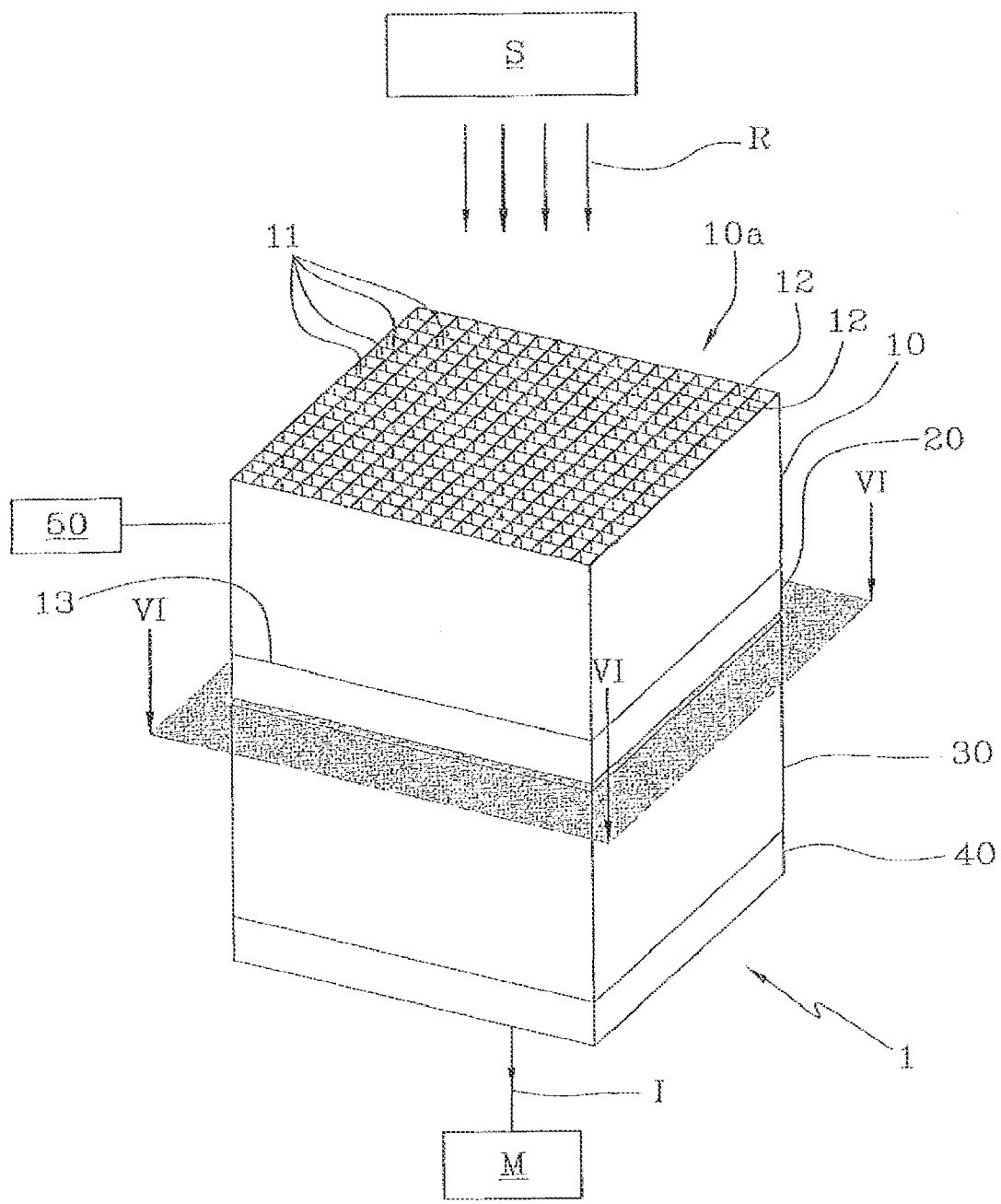
FIG. 1 diagrammatically shows a scintigraphic device in accordance with the present invention.

With reference to the drawings a scintigraphic device according to the present invention has been generally identified by reference numeral 1.

Device 1 can be for instance used in the scintigraphic analysis of small animals, for the purpose of experimenting with new radio-marked antibodies, specific for determined pathologies.

This device can also apply in Astrophysics and in arrangements for non-destructive controls of the industrial type, as well as in Nuclear Medicine as a location and diagnostic device both in SPECT and PET techniques.

The scintigraphic device 1 (FIG. 1) first of all comprises a collimator 10 provided with an inlet 10a for receiving the electromagnetic radiation R coming from a predetermined source S and selecting the radiation directed towards a scintillation structure 20.

This electromagnetic radiation R can be for example a gamma radiation coming from the object or the body to be examined. In particular, the function of collimator 10 is to enable passage of the only radiation directed perpendicular to the scintillation structure 20 (to be better described in the following), shielding every type of radiation coming from different directions.

It is to be noted that gamma rays (photons) cannot be deviated by optical lenses, as it happens for light photons in traditional photography for example, due to the penetrating power of these rays, and to the fact that they are substantially devoid of any electric charge. The photon beam is therefore modulated by means of collimator 10 the action of which consists in shielding most of the photons emitted by source S.

Advantageously, collimator 10 comprises a plurality of equal conduits 11 of predetermined length, identified and separated by septa 12 of a thickness suitable for the photon energy to be detected, which terminate in a common end plane 13 on the side opposite to said source S, i.e. on the opposite side relative to inlet 10a.

Preferably, collimator 10 is made of a material having a high effective atomic number ($Z_{eff}$) and high density, such as tungsten, lead, gold, tantalum, palladium, etc. This material is therefore provided with a high power of attenuation, so as to attenuate the intensity of the radiation from space regions that are not included in the solid angle intercepted by the collimator's inlet 10a. By way of example, in one embodiment, the penetration factor of septa 12 is lower than 0.7%, and collimator 10 has an overall parallelepiped shape with a square base of 50 mm×50 mm (see the diagrammatic representation in FIG. 1).

As mentioned above, device 1 further comprises a scintillation structure 20 associated with collimator 10 for receiving said electromagnetic radiation R and converting it into visible radiation V.

Preferably, the scintillation structure 20 is positioned at said common plane 13. Preferably the scintillation structure 20 comprises a plurality of scintillation crystals 21 (FIG. 5), each of them substantially matching the shape of the end 14 of a respective conduit 11 of said collimator 10. More particularly, crystals 21 are each mounted on an end 14 of the respective conduit 11, so as to form the common end plane 13.

In the preferred embodiment, each conduit 11 and each crystal 21 have a substantially square cross-section.

Preferably, the scintillation crystals 21 can be of the inorganic or organic type, either in the hyperpure state or doped with suitable amounts of appropriate materials in order to enhance the scintillation features thereof (for instance CsI (Tl), CsI(Na), NaI(Tl), $LaCl_3$:Ce, $LaBr_3$:Ce, BGO, LSO, etc.) depending on the type of application to be put into practice, the diagnostic techniques and the tracers used. At all events the emission spectrum of the scintillation light must have a good superposition with the absorption spectrum of the photosensitive layer of the electro-optical converter 30, to be described in the following.

Figure 5:
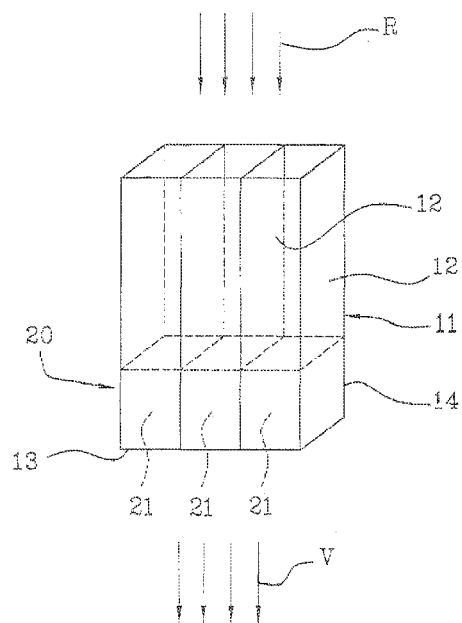
FIG. 5 shows details of the apparatus in FIG. 1.

FIG. 5 shows only three conduits 11, for the sake of simplicity, and the related scintillation crystals 21; each of conduits 11 of collimator 10 preferably has the structure shown in FIG. 5.

As mentioned above, device 1 further comprises an electro-optical converter 30, associated with the scintillation structure 20 for receiving said visible radiation V and converting it into electric signals E.

The electro-optical converter 30 may for instance comprise phototubes, photodiodes, APD (Avalanche Photo Diode), MPPC (Multi-Pixel Photon Counter), direct use of semiconductors, etc.

In the preferred embodiment, converter 30 comprises a plurality of phototubes 31 disposed in mutual side by side relationship, the physical sizes of these phototubes 31 being generally non-coincident with their active area. This involves the existence of several "dead regions" between the active areas of the detector. In fact, in this specific case, the scintillation structure 20 is made up of several blocks 20a, each coupled to a single phototube 31. The whole detection area is determined by the assembly of said scintillation blocks constituting structure 20. The "dead region", of sizes Ds (FIG. 6) represents the distance between the individual scintillation blocks of structure 20.

This dead region Ds is generally very restrained, but can reasonably be practically considered as zero or reduced through some solutions such as those described in the aforesaid U.S. Pat. No. 6,608,310 (Soluri et al.).

Figure 6:
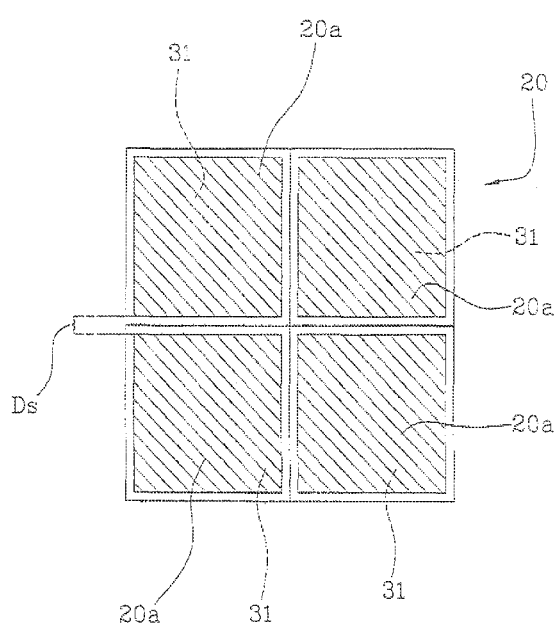
FIG. 6 diagrammatically shows a partial sectional view of the device in FIG. 1 taken along line VI-VI, concerning the scintillation structure 20.

Shown in FIG. 6 is a scintillation structure 20 relating to a detector only made up of four phototubes 31; converter 30 at all events can also comprise any greater number of phototubes.

Advantageously, converter 30 is associated with a suitable electronic operation circuitry determining the position and energy of the event, converting this information into a digital format and transferring it to the processing unit 40 to be described in the following.

As mentioned above, the scintigraphic device 1 further comprises a processing unit 40 connected to the electro-optical converter 30 for receiving said electric signals E and, depending on said signals, rebuilding images representative of the predetermined source S.

Practically, the processing unit 40 is designed to supply an operator, by a display or monitor M for example, with a digital representation of source S, obtained through the above described detection operations and transmissions.

The operations performed by the processing unit 40 will be described in more detail in the following of the present discussion.

Device 1 further comprises an actuating system 50 for mutually moving the predetermined source S and at least collimator 10, to enable collimator 10 to detect the electromagnetic radiation R at different mutual positioning locations of the predetermined source S and of collimator 10.

In case of use of a single planar crystal as the scintillation structure 20, movement of collimator 10 alone is preferable; on the contrary, should the scintillation structure 20 comprise a crystal matrix, movement of the whole scintillation structure 20 is preferable, or joint and firm movement of the scintillation structure 20, converter 30 and collimator 10.

Practically, the actuating system 50 comprises one or more actuators 51 (FIG. 2) to move collimator 10 relative to the predetermined source S. Preferably, collimator 10, scintillation structure 20 and electro-optical converter 30 are substantially integral with each other; therefore, the actuating system 50 is advantageously adapted to substantially simultaneously and jointly move collimator 10, scintillation structure 20 and electro-optical converter 30.

Generally, collimator 10 and the different elements rigidly connected therewith form a detection head 2.

Figure 2:
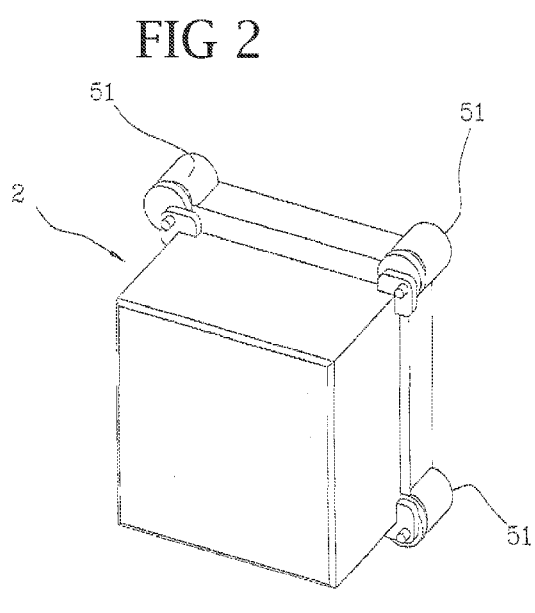
FIG. 2 diagrammatically shows some details of the device of the invention, with some parts removed for a better view of others.
Figure 2A:
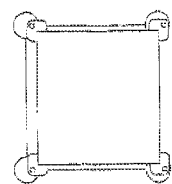
FIGS. 2a-2d show possible operating configurations of the device of the invention.
Figure 2B:
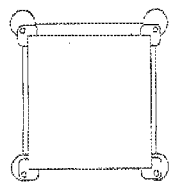
Figure 2C:
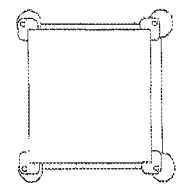
Figure 2D:
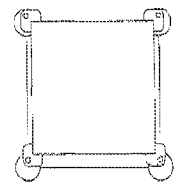

As diagrammatically shown in FIG. 2, the actuating system 50 can comprise four actuators 51 for example, each of them acting on a respective angular portion of the detection head 2; by way of example, FIGS. 2a-2d show four possible operating configurations obtained as a result of movement caused by actuators 51.

Actuators 51 can be electric motors (e.g. brushless motors), for example.

In addition or alternatively, actuators 51 can be of the piezoelectric or pneumatic type or step-by-step motors, etc.

In a possible embodiment, actuators 51 are mounted on device 1 and are substantially rigidly connected therewith.

In an alternative embodiment, actuators 51 are mounted externally of device 1 so that they can act thereon and cause the described movements.

Due to the above disclosed structure, device 1 is able to detect a plurality of images different from each other, of the same source S.

Advantageously, the actuating system 50 can be interlocked with the processing unit 40 so as to synchronize movement of the detection head 2 and the processing operation leading to obtaining representative images of source S.

The processing unit 40 is therefore adapted to rebuild a plurality of auxiliary images I1-I4 representative of such a source S; each auxiliary image, in particular, corresponds to a respective mutual positioning of collimator 10 relative to source S. In other words, if source S is supposed to be substantially "immobile" i.e. rigidly fixed to the ground, collimator 10 (generally the detection head 2) is moved to several positions different from each other; at each position, i.e. at each mutual positioning between collimator 10 and source S, the radiation R emitted by source S is detected and therefore respective auxiliary images I1-I4 are rebuilt by the processing unit 40, one image for each mutual position (FIGS. 4a-4d).

Displacement of the auxiliary images I1-I4 relative to source S is therefore shown in FIGS. 4a-4d.

The processing unit 40 is also adapted to generate a final image I as a function of the auxiliary images I1-I4.

More particularly, the final image I has a spatial resolution the numeric value of which is smaller than that of the spatial resolution of the auxiliary images I1-I4.

In fact, an intrinsic spatial resolution of device 1 being defined, the auxiliary images I1-I4 have a spatial resolution the numeric value of which is not numerically less than that of the intrinsic spatial resolution of device 1.

In the present context and in the following claims, by spatial resolution it is intended the minimum size that can be detected by a device and/or reproduced into an image; in other words, if a device has a spatial resolution of "r", expressed in millimeters for example, this device is not able to distinguish and/or reproduce smaller sizes of "r".

Therefore, an image the spatial-resolution numeric value of which is high, will be an image with a reduced precision, represented by large "pixels". This case is defined as a "low-spatial-resolution" image, which term means the low information contents present therein.

On the contrary, an image the spatial-resolution numeric value of which is low, will be a very precise image, represented by "small" pixels. This case is defined as a "high-spatial-resolution" image, which term means the high information contents present therein.

Originating from these definitions, a "low-resolution space" is a space in which low-spatial-resolution images are represented. On the contrary, a "high-resolution space" is a space in which high-resolution images are represented.

The intrinsic spatial resolution of the scintigraphic device 1 can be defined as the sum of the contributions connected to the choice of the crystal and the opto-electronic device (i.e. the electro-optical converter 30) or, in case of a semi-conductor system, is connected to the sizes of the individual detection element.

In the context of the present invention, both the intrinsic spatial resolution of device 1 and the total spatial resolution defined by the relation below can be taken as a reference:

$$R_S = \sqrt{R_i^2 + R_c^2}$$

wherein:

$R_i$ represents the intrinsic spatial resolution, and $R_c$ represents the contribution of collimator 10 in terms of spatial resolution.

In other words, the displacements to be carried out by the actuating system 50 and the processing operations to be performed on the auxiliary images I1-I4 can be determined in an advantageous manner by considering either the intrinsic spatial resolution or the total spatial resolution.

Preferably, each conduit 11 has a major longitudinal extension, preferably defined by the direction orthogonal to the inlet 10a and/or to the end plane 13 of collimator 10; the section orthogonal to this extension, in case of use of a scintillation matrix, is substantially square. Generally, the intrinsic resolution of device 1 has a close correlation with the side sizes of this square.

It is to be pointed out that the intrinsic spatial resolution of the scintigraphic device 1 is in principle independent of the graphic resolution by which the images rebuilt by the processing unit 40 are then displayed for the operator; in other words, the intrinsic resolution of device 1 depends on the construction features of the device itself and is not connected with the resolution of the monitor or screen M on which the digitally rebuilt images are displayed.

In more detail, with reference to said auxiliary images I1-I4, each auxiliary image I1-I4 represents at least part of the same portion of source S also represented by at least another auxiliary image.

In other words, given a certain auxiliary image, said image will have the representation of at least one portion of source S of the radiation R in common with one or more of the other auxiliary images. Practically, each auxiliary image will be almost fully superposed on the other auxiliary images, so that each of them can bring a useful information contribution to rebuilding of the final high-resolution image.

In this way, as better clarified in the following, by virtue of this amount of detected information, it will be possible to improve the resolution for representation of the predetermined source S. In particular, each auxiliary image is correlated with one or more of the other auxiliary images that appear to be superposed on this auxiliary image; the superposed auxiliary images contain information relating to source S as a function of the displacement carried out.

Superposed images are obtained, as mentioned above, through displacement of collimator 10, possibly in combination with the scintillation structure 20 and converter 30, relative to source S; preferably each of the auxiliary images I1-I4 represents at least one and the same portion of source S.

In more detail, each auxiliary image I1-I4 fully represents the radiation source S; in fact, each individual auxiliary image I1-I4, obtained with low spatial resolution, contains most of the information concerning source S.

Preferably, superposed single auxiliary images in succession are obtained by moving the detection head 2 in substantially orthogonal directions.

Should the auxiliary images I1-I4 have a substantially square or rectangular conformation, movement of the detection head 2 can take place in directions parallel to the sides of said images. Preferably, superposed auxiliary images are spaced apart a lower distance than the intrinsic spatial resolution of device 1. Preferably, the distance between superposed auxiliary images is greater than the thickness of said septa 12.

In addition, should the electro-optical converter 30 comprise a plurality of phototubes 31, the superposed images are spaced apart a greater distance than the separation distance Ds of the dead regions (FIG. 6).

In more detail, the auxiliary images I1-I4 are arranged in succession, in rows or columns for example.

Each auxiliary image therefore has a preceding or following auxiliary image superposed thereon according to said arrangement and is spaced apart from said preceding or following auxiliary image by a distance D smaller than the (intrinsic or total) spatial resolution of device 1.

Preferably, this distance D is a sub-multiple of the (intrinsic or total) spatial resolution of device 1.

As above said, distance D is advantageously greater than distance Ds, and is greater than the thickness of septa 12.

Figure 4A:
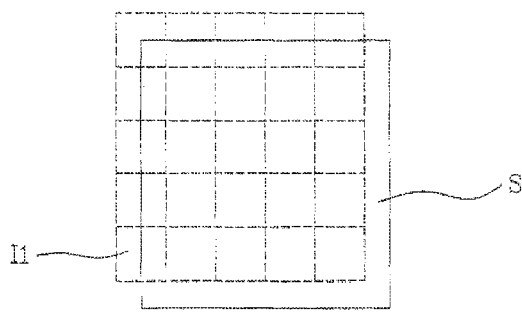
FIGS. 4a-4d diagrammatically show images obtained through movement of the device of the invention and used in the processing operations of said device.
Figure 4B:
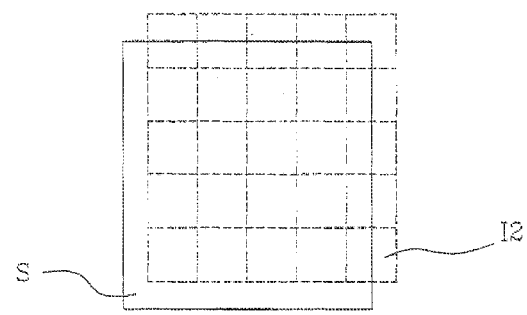
Figure 4C:
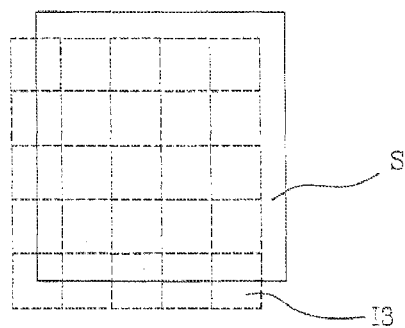
Figure 4D:
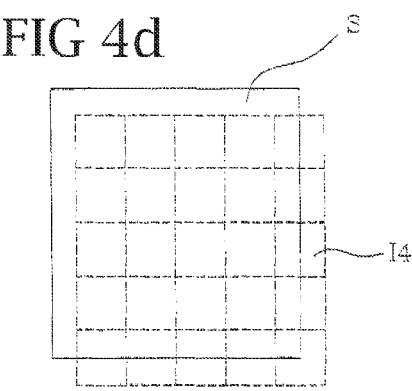

Preferably, distance D can be estimated along the directions defining the sides of the auxiliary images I1-I4; each auxiliary image can have a distance D from the preceding or following image both along axis X and along axis Y (see FIG. 4c, for example).

By way of example only, a device 1 having a spatial resolution of 2.4 mm can be considered. In other words, the cross section of conduits 11, as well as the side of the scintillation crystals 21 is equal to 2.4 mm.

If no processing of the detected images were provided, source S could not be represented, downstream of the processing unit 40, with a spatial resolution the numeric value of which were smaller than the intrinsic spatial resolution of device 1; this means that pixels representing source S of radiation R could not have sizes smaller than 2.4 mm.

On the contrary, by applying the present method with displacements of an amount smaller than 2.4 mm, equal to 1.2 mm for example, it is possible to detect said auxiliary images I1-I1 and improve spatial resolution by a factor of 2. Therefore, four auxiliary images I1-I4 would be detected for example, each spaced apart 1.2 mm from the images adjacent thereto and superposed thereon, as diagrammatically shown in FIGS. 4a-4d.

By way of example, FIGS. 4a-4d represent the auxiliary images detected at the respective positions of the detection head 2 shown in FIGS. 2a-2d. Therefore, if auxiliary images I1-I4 are detected which however have a low spatial resolution (equal to 2.4 mm, for example), spaced apart 1.2 mm from each other, a final image I having a high spatial resolution equal to 1.2 mm can be obtained.

In spite of the fact that reference has been made to detection of four auxiliary images I1-I4 (diagrammatically shown in FIGS. 4a-4d), it is possible to choose an arbitrary number of auxiliary images to be detected, preferably a number that is a perfect square number, depending on the features of device 1, the processing unit 40 and the required final resolution.

In order to obtain the final image I as a function of the auxiliary images I1-I4, algorithms based on a Bayes approach or techniques based on transforms of the wavelet-type can be for example used.

As to movements of the detection head 2, different possibilities for detection of the auxiliary images I1-I4 are provided.

According to a first embodiment, head 2 is positioned and maintained immobile in each of the positions at which an auxiliary image is detected.

Alternatively, the detection head 2 is handled/moved in a continuous manner, i.e. without being stopped in each position and then moved again for reaching the following position, and detection carried out by the detection head 2 and processing unit 40 is substantially continuous; the processing unit 40 itself then detects, within the "movie" thus obtained, the auxiliary images I1-I4 which are identified being for example "a priori" known the time instant at which the detection head 2 is in the different positions of interest.

Figure 3A:
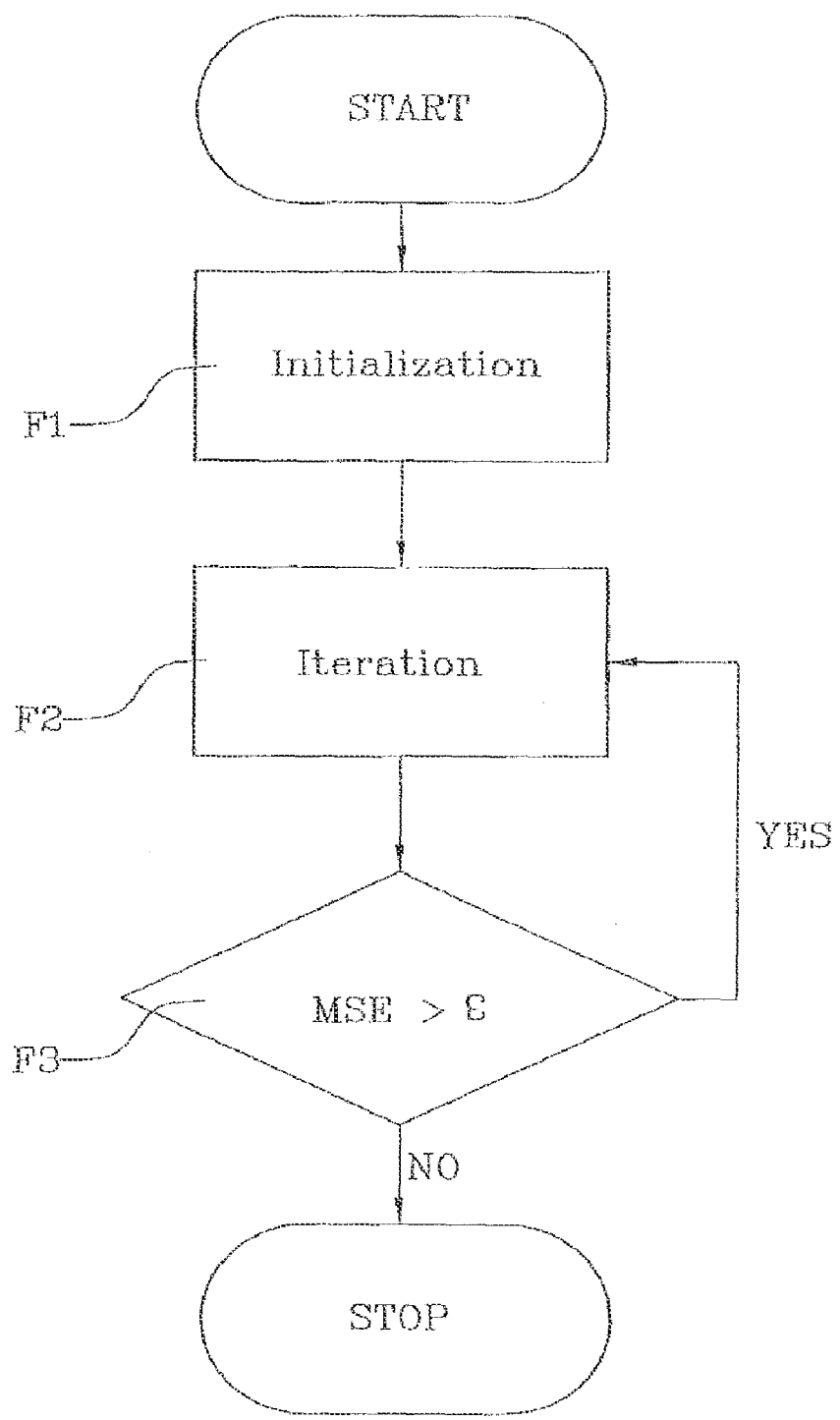
FIG. 3a is a flow diagram summarizing the processing operations performed by the device of the invention.

By way of example, FIG. 3a shows a possible embodiment of the algorithm used for operation of device 1.

After a starting step, initialization of data is carried out and an initial estimate of the high resolution image is done (step F1).

Then an iteration step is carried out in which estimate of the image is made up-to-date (step F2), as well as a control step (step F3) at which the error amount is estimated in order to establish whether the iterative cycle is to be interrupted or not.

More particularly, the Medium Square Error (MSE) quantifies the difference between the estimated high-resolution final image I at the end of the current estimate and the final image I estimated in the preceding iteration; the cycle is completed when the error amount is smaller than a predetermined threshold $\epsilon$:

$$MSE = \frac{1}{N}\|I_n - I_{n-1}\|^2$$

wherein:
n is the current step;
$I_n$ is the current iteration;
$I_{n-1}$ is the preceding iteration;
N is the number of the image elements.

Figure 3B:
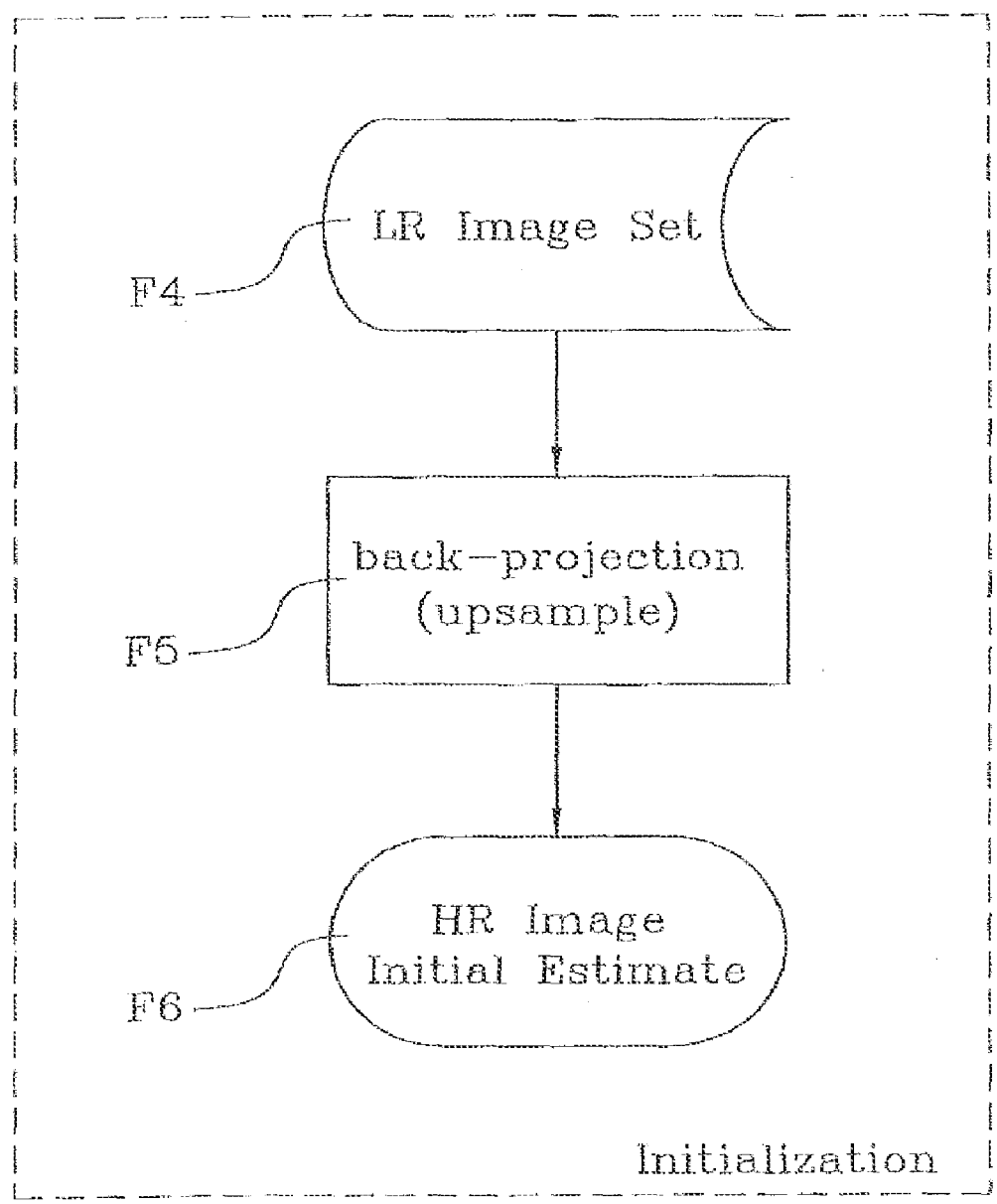
Figure 3C:
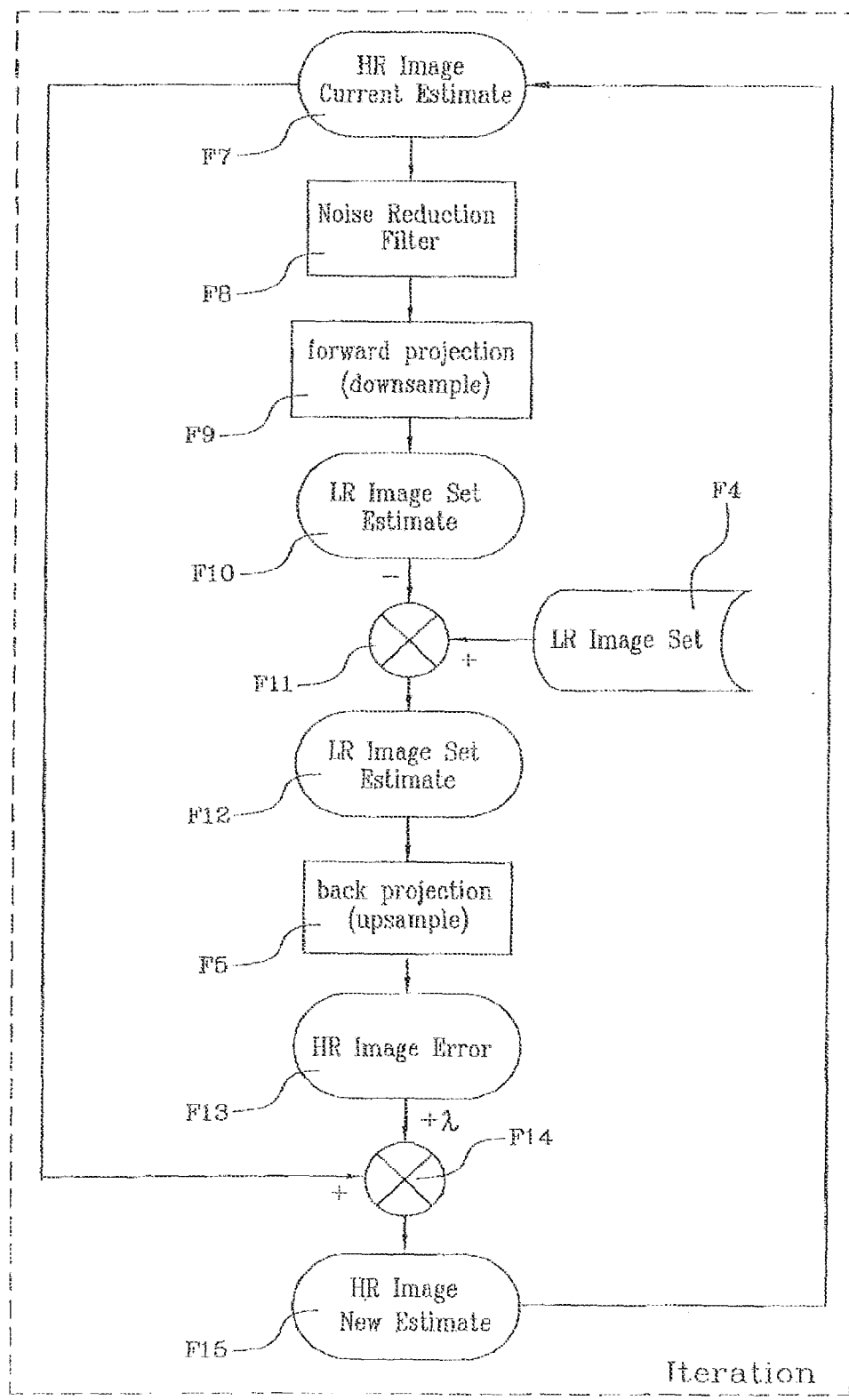

In more detail (FIG. 3b), step F1 for data initialization starts from the auxiliary low spatial resolution image set (i.e. of the same resolution as the intrinsic resolution of device 1) and involves a "projection" of the low spatial resolution data on a high spatial resolution space, based on the "position" of each auxiliary image. Therefore, from the auxiliary images, a high resolution image is obtained.

By the term "projection" it is intended a new data sampling, starting from a given spatial resolution space to a space of different spatial resolution. The new sampling can take place either downwards (from high to low spatial resolution) or upwards (from low to high spatial resolution) by suitable algorithms such as decimation (downwards) or interpolation (upwards).

The initialization step F1 finally comprises an estimate sub-step for estimation of the spatial high-resolution image.

As to the above mentioned iterative cycle, it can comprise the following sub-steps:
F7: estimate of the high resolution image for current iteration;
F8: filtering for noise reduction; use can be made for example of an adaptive filter, a Wiener filter, an optimal filter for a definite noise figure;
F9: projection of the data contained in the high resolution image onto the low resolution space, as a function of the distance from the starting image; thus from the high resolution image, a low resolution image set is obtained;
F10: estimate of the low resolution images for current iteration;
F11: difference operation between the detected low-resolution image set and the estimated images, so as to obtain an error estimate;
F12: error estimate in the low resolution space;
F13: error estimate in the high resolution space;
F14: addition operation of the high resolution image and the error relating to the high resolution space weighed through a relaxation parameter $\lambda$;
F15: new estimate of the high resolution image.

The invention achieves important advantages.

First of all, the device of the invention allows images with a better spatial resolution to be obtained as compared with that imposed by the physical and construction limits of the device itself.

In particular, the method advantageously has no incidence on the initial hardware configurations determining some physical parameters of the device but it only operates on the modalities by which the images are acquired and the subsequent image processing.

Another advantage resides in that the device of the invention allows the spatial resolution of the images obtained to be improved without resorting to modifications or replacements in the starting detection structure.

A further advantage is represented by the fact that the device is able to carry out detection operations with different resolutions, without substantial modifications being needed for the device itself.

What is claimed is:

1. A scintigraphic device comprising:
    a collimator (10) for receiving and selecting the electromagnetic radiation (R) from a predetermined source (S);
    a scintillation structure (20) associated with the collimator (10) for receiving said electromagnetic radiation (R) from said collimator (10) and converting it into visible radiation (V);
    an electro-optical converter (30) associated with said scintillation structure (20) for receiving said visible radiation (V) and converting it into electric signals (E);
    a processing unit (40) connected to said electro-optical converter (30) for receiving said electric signals (E) and rebuilding, as a function of said electric signals (E), images of said predetermined source (S);
    an actuating system (50) for mutually moving said predetermined source (S) and at least said collimator (10), to enable said collimator (10) to detect said electromagnetic radiation (R) at different mutual positioning locations of said predetermined source (S) and said collimator (10), said processing unit (40) being adapted to rebuild a plurality of auxiliary images (I1-I4) representative of said predetermined source (S), each auxiliary image (I1-I4) corresponding to a respective mutual positioning of said predetermined source (S) and said collimator (10), said processing unit (40) being adapted to generate a final image (I) as a function of said auxiliary images (I1-I4), wherein said final image (I) has a spatial resolution the numeric value of which is smaller than the spatial resolution of said auxiliary images (I1-I4).

2. The device as claimed in claim 1, wherein said collimator (10) comprises a plurality of equal conduits (11) of predetermined length, identified and separated by septa (12) of a thickness suitable for the photon energy to be detected, which terminate in a common end plane (13) on the side opposite to said source (S); said scintillation structure (20) being positioned at said common plane (13).

3. The device as claimed in claim 2, wherein said scintillation structure (20) comprises a plurality of scintillation crystals (21), the shape of each of them substantially matching that of the end (14) of a respective conduit (11) of said collimator (10).

4. The device as claimed in claim 3, wherein each of said crystals (21) is mounted on one end (14) of the respective conduit (11) of said collimator (10), so as to form said common end plane (13).

5. The device as claimed in claim 3, wherein said scintillation structure (20) is separated from said collimator (10) and faces the latter at said end plane (13).

6. The device as claimed in claim 2, wherein each of said auxiliary images (I1-I4) is associated with at least one respective auxiliary image superposed thereon, and is displaced relative to the latter by a greater distance than the thickness of said septa (12).

7. The device as claimed in claim 1, wherein said scintillation structure (20) comprises a single substantially planar scintillation crystal the shape of which matches that of an outer profile of said collimator (10).

8. The device as claimed in claim 1, wherein said scintillation structure (20) comprises a plurality of semiconductor elements.

9. The device as claimed claim 1 wherein, an inherent resolution of said device (1) being defined, said auxiliary images (I1-I4) have the same resolution as said inherent resolution, and said final image (I) has a spatial resolution the numeric value of which is smaller than said inherent resolution.

10. The device as claimed in claim 9, wherein each of said auxiliary images (I1-I4) is associated with at least one respective auxiliary image superposed thereon, and is displaced relative to the latter by a smaller distance than the inherent resolution of said device (1).

11. The device as claimed in claim 1, wherein each of said auxiliary images (I1-I4) represents at least part of the same portion of said predetermined source (S) also represented by at least another auxiliary image.

12. The device as claimed in claim 11, wherein each of said auxiliary images (I1-I4) is associated with at least one respective auxiliary image superposed thereon, and is displaced relative to the latter by a smaller distance than the inherent resolution of said device (1).

13. The device as claimed in claim 1, wherein each of said auxiliary images (I1-I4) substantially represents the whole predetermined source (S).

14. The device as claimed in claim 1, wherein said electro-optical converter (30) comprises a plurality of phototubes (31) or photodiodes disposed in side by side relationship with each other, each of said auxiliary images (I1-I4) being associated with at least one respective auxiliary image superposed thereon, and being displaced relative to the latter by a distance greater than a separation distance (Ds) defined between the active areas relating to the scintillation blocks (20a).

15. The device as claimed in claim 1 wherein said actuating system (50) comprises at least one actuator (51) mounted on said device (1) and substantially integral therewith.

16. The device as claimed in claim 1, wherein said actuating system (50) comprises at least one actuator (51) mounted externally of said device (1) and acting thereon for mutual movement of the collimator (10) and said source (S).

* * * * *